United States Patent

Sakaguchi et al.

[11] Patent Number: 5,860,927
[45] Date of Patent: Jan. 19, 1999

[54] DIAGNOSTIC ULTRASOUND DOPPLER IMAGING SYSTEM AND DOPPLER IMAGING METHOD FOR ULTRASONIC DIAGNOSIS

[75] Inventors: Fumiyasu Sakaguchi; Masao Takimoto; Akihiro Sano, all of Otawara, Japan

[73] Assignee: Kabushiki Kaisha Toshiba, Kawasaki, Japan

[21] Appl. No.: 867,815

[22] Filed: Jun. 3, 1997

[30] Foreign Application Priority Data

Jun. 4, 1996 [JP] Japan .................................. 8-141715

[51] Int. Cl.⁶ ........................................................ A61B 8/00
[52] U.S. Cl. ................................................................ 600/453
[58] Field of Search .................................. 600/443, 440, 600/441, 449, 453

[56] References Cited

U.S. PATENT DOCUMENTS

| | | | |
|---|---|---|---|
| 5,241,473 | 8/1993 | Ishihara et al. | 600/443 |
| 5,419,328 | 5/1995 | Goh et al. | 600/443 |
| 5,531,224 | 7/1996 | Ellis et al. | 600/443 X |
| 5,533,510 | 7/1996 | Koch, III et al. | 600/443 |
| 5,615,680 | 4/1997 | Sano | 128/661.09 |
| 5,622,174 | 4/1997 | Yamazaki | 128/661.09 |

OTHER PUBLICATIONS

R.M. Lang et al., "Echocardiographic Quantification of Regional Left Ventricular Wall Motion With Color Kinesis", Circulation, 93(10):1877–1885.

*Primary Examiner*—Francis J. Jaworski
*Attorney, Agent, or Firm*—Finnegan, Henderson, Farabow, Garrett & Dunner, L.L.P.

[57] ABSTRACT

In order to enable quantitative and ready assessment of the kinetics of a tissue on the basis of motion information of the tissue resulting from analysis performed according to the Doppler method, and to enable ready observation of a temporal change in motion of the tissue, there is provided, as one aspect, a diagnostic ultrasound Doppler imaging system. The system comprises a unit for scanning an object with ultrasonic waves over a cross section of the object to produce an echo signal representing electrical quantities proportional to ultrasonic waves reflected from the object; a unit for extracting from the echo signal a Doppler signal emanating from a tissue in motion inside the object; and a unit for analyzing the frequency of the Doppler signal to obtain two-dimensional image data concerning the motion of the tissue on the cross section frame by frame. The system further comprises a unit for superposing a plurality of old and new frames of the two-dimensional image data computed time-sequentially; and a unit for displaying the superposed two-dimensional image data. The displaying unit includes a circuit for coloring the superposed two-dimensional image data according to the motion of the tissue.

20 Claims, 9 Drawing Sheets

PRIORITY GIVEN TO OLD IMAGES
FIG. 3A

PRIORITY GIVEN TO NEW IMAGES
FIG. 3B

PRIORITY GIVEN TO OLD IMAGES
FIG. 3C

PRIORITY GIVEN TO NEW IMAGES
FIG. 3D

DIAGNOSTIC ULTRASOUND DOPPLER IMAGING SYSTEM AND DOPPLER IMAGING METHOD FOR ULTRASONIC DIAGNOSIS

BACKGROUND OF THE INVENTION

1. Field of the Invention

The present invention relates to a diagnostic ultrasound Doppler technology enabling effective diagnosis of ischemic cardiac diseases including myocardial infarction and angina, and left ventricular dilation including hypertrophic cardiomyopathy. More particularly, this invention is concerned with tissue Doppler imaging (TDI) in which a Doppler imaging method is used to detect motion information of a cardiac muscle (cardiac wall) or vascular wall, and the results of computation are displayed in color.

2. Description of the Related Art

Currently, quantitative assessment of cardiac or vascular functions is essential to diagnosis of cardiac diseases. Various methods of diagnosis have been attempted.

Ultrasonic diagnosis that is one of such methods is often achieved by observing a real-time B-mode tomographic image of, for example, the left ventricle (the left ventricle is regarded as a center of assessment of cardiac functions). Through observation, a grave symptom of an ischemic cardiac disease, left ventricular dilation, or the like can be diagnosed to some extent.

In recent years, more advanced and specialized diagnostic methods have been proposed. For example, there is left ventricular wall motion analysis dedicated to diagnosis of ischemic cardiac diseases. This analytic method measures change in thickness of a cardiac muscle between a left ventricular systole and diastole, and a region exhibiting a small change in thickness is diagnosed as a "region with a deteriorated contracting ability," that is, an "ischemic region." Various algorithms have been devised for this analysis. Whichever of the algorithms is adopted, a B-mode tomographic image is used to trace the contour of the left ventricular endocardium or epicardium at an end systole and end diastole. The trace information is used for measurement.

Stress echo imaging is also known as a method for diagnosing myocardial infarction. This diagnostic method stresses the heart through exercise, by administering a drug, or by applying an electrical impulse. Ultrasonic tomographic (B-mode) images of the heart produced before and after the stressing are recorded. Thereafter, the images produced before and after the stressing are displayed side by side on one monitor and are compared with each other in terms of change in thickness of a cardiac muscle between a cardiac systole and diastole (cardiac muscles normally thicken during a systole). Thus, a region with infarction can be specified.

However, the foregoing diagnostic methods have various drawbacks such as those described below.

To begin with, when a B-mode tomographic image is viewed and observed for diagnosis, because a monitor screen displays a mere real-time image, it is hard to determine hypofunction of an organ or discriminate an abnormal tissue. Even for a physician having abundant experience in ultrasonic diagnosis, it is practically hard to acquire detailed information of a region with a locally-deteriorated contracting ability deriving from an ischemic cardiac disease, or of left ventricular dilation. Moreover, the left ventricular wall motion analysis is a diagnostic method dedicated to ischemic cardiac diseases, and therefore lacks in generality.

Under these circumstances, a first relatively useful approach is an approach using a tissue Doppler imaging (TDI) system. Using this system, a Doppler signal is extracted from an echo signal on which the motion of a tissue such as a cardiac muscle is reflected, and motion velocity information resulting from frequency analysis of the Doppler signal is displayed as a color tomographic image. The color tomographic image is displayed while being updated sequentially frame by frame, or displayed as a frozen image.

Furthermore, as a second approach, an approach using a diagnostic ultrasound system in which tracing the contour of a tissue and coloring are combined for imaging has been known in the past (for example, Roberto M. Lan et al., "Echocardiographic Qantification of Regional Left Ventricular Wall Motion With Color Kinesis", 1877–1885, Vol. 93, No. 10, May 15, 1996). Taking a cardiac muscle for instance, the contour of the endocardium is traced in each of frames constituting a B-mode tomographic image (black-and-white) produced during a systole, and areas defined with pairs of contour lines are colored differently for display. Consequently, the endocardium is seen making motion in real time with contraction.

However, the foregoing first and second approaches still have the drawbacks described below.

The tissue Doppler imaging system employed in the first approach displays only a Doppler image of a tissue at a certain instant, and is therefore unsuitable for observing a time-sequential change in motion. When a tissue Doppler image is used to assess the cardiac or vascular functions, compared with when a B-mode image is viewed or observed, it is advantageous that velocity information can be observed directly. For determining hypofunction of an organ or discriminating an abnormal region, it takes much time and labor for handling. Moreover, the determination or discrimination still requires expertise and is therefore hard to do.

In the case of the system employed in the second approach, in which tracing a contour in a B-mode image and coloring are combined, there are the drawbacks described below.

First, image information used for imaging is B-mode morphologic information and therefore lacks in motion information of each myocardial region. For example, areas defined pairs of contours of the endocardium in frames are painted in the same color, and the morphology of the endocardium making a time-sequential change in motion is thus expressed. Resultant diagnosis is analogous to that in the foregoing left ventricular analysis, and is achieved by detecting an abnormality such as myocardial infarction through interpretation of a morphologic change of the endocardium. Unless an illness progresses and becomes considerably grave, an apparent morphologic change is usually not discerned. This kind of diagnostic method is therefore unsuitable for early discovery of an illness or discovery of an illness in an early stage.

Secondly, there is a problem with precision in tracing the contour of the endocardium. As mentioned above, if discovery of an abnormal region is dependent only on a morphologic change of the endocardium, the precision in tracing the contour of the endocardium counts. If the precision deteriorates, it would presumably lead to misdiagnosis or missing an abnormal region. Eventually, the reliability of the system deteriorates.

SUMMARY OF THE INVENTION

The present invention attempts to solve the foregoing drawbacks underlying the prior art. A major object of the present invention is to provide a method of ultrasonic diagnosis enabling quantitative and ready assessment of the kinetics of a tissue.

Another object of the present invention is to enable quantitative and ready assessment of the kinetics of a tissue on basis of the motion information of the tissue resulting from analysis performed according to the Doppler method.

Yet another object of the present invention is to enable ready observation of a temporal change in motion of a tissue.

For accomplishing the above objects, one aspect of the present invention includes a diagnostic ultrasound Doppler imaging system in which a plurality of successive frames of two-dimensional image data reflecting Doppler shifts caused by a tissue in motion in a cross-section of an object being imaged are obtained by scanning ultrasonic signals along the entire cross-section, the system including means for adaptively superposing at least two of the plurality of successive frame by frame; means for superposing a plurality of old and new frames of the two-dimensional image data one on another so that time-sequential information among the plurality of successive frames is present; and means for displaying the superposed two-dimensional image data.

Preferably, the displaying means includes means for coloring the superposed two-dimensional image data according to a motion direction of the tissue. In this case, it is preferred that the system comprises means for producing a reference signal indicative of the motion of the tissue of the object, wherein said superposing means includes means for performing a superposition process of at least two of the plurality of successive frames in synchronization with the reference signal. For example, the tissue is a cardiac muscle of a heart of the object and the reference signal is a timing signal corresponding to a specified time instant in an electrocardiogram signal wave of the heart. Preferably, the performing means is means that performs the superposition process during at least one of systole and diastole of the cardiac muscle a specified interval synchronous with the timing signal.

Further it is preferred that the superposing means includes means for controlling the superposition process so that at least two of the plurality of successive frames of the two-dimensional image data is adaptively superposed on one another on the basis of an algorithm that pixels representing the tissue and existing only in either one of a new superposing frame selected from the plurality of successive frames and an old frame to be superposed which has been formed by any of the plurality of successive frames remain as the pixels are in the superposed two-dimensional image data, and pixels representing the tissue and commonly existing in the new and old frames selectively remain in the superposed two-dimensional image data on a superposing priority order according to either one of a temporal ascending order and a temporal descending order of the plurality of successive frames. As one example, said superposition process controlling means includes a weighting circuit for performing weighting by multiplying pixel by pixel each of the successive old frames of two two-dimensional image data by a weighting coefficient determined depending on the algorithm. The weighting coefficients, for example, consist of two coefficients, 1 and 0.

It is also preferred that the superposing means comprises means for previously storing a plurality of superposition modes for the superposition process defined on the basis of characteristics of a motion direction and a section shape of the tissue in the cross-section of the object, and means for selecting a desired one from the plurality of superposition modes. In this case, preferred is that the plurality of superposition modes depend on a superposing priority order according to either one of a temporal ascending order and a temporal descending order among the plurality of successive frames of two-dimensional image data. Still, preferred is that the tissue is a cardiac muscle of a patient as the object and the plurality of superposition modes comprising a first superposition mode giving priority of the superposition process to endocardium of the cardiac muscle systole thereof, a second superposition mode giving a priority of the superposition process to endocardium of the cardiac muscle during the systole thereof, a third superposition mode giving priority of the superposition process to the endocardium of the cardiac muscle during diastole thereof cardiac, and a fourth superposition mode giving priority of the superposition process to the endocardium of the cardiac muscle during diastole thereof. Preferably, the storing means consist of means for previously storing a plurality of superposition patterns made by combining at least any two modes selected from the first to fourth superposition modes for one cardiac cycle ranging from the systole to the diastole of the cardiac muscle.

Furthermore, it is preferred that the superposing means consist of means for performing the superposition process with obtaining time phase information representing acquired time instants of the plurality of successive frames, and the system further comprises means for movably setting a ROI (region of interest) on an image displayed by the displaying means, and means for obtaining the time phase information associated with an image frame providing pixels on which the ROI is set. Preferred is that the time phase information is numbers representing a time-sequential order of the frames of the two-dimensional image data superposed by the superposing means and the displaying means includes means for displaying the numbers together with the superposed two-dimensional image data.

According to another aspect of the present invention, there is provided a method of Doppler imaging for ultrasonic diagnosis in which a plurality of successive frames of two-dimensional image data reflecting Doppler shifts caused by a tissue in motion in a cross section of an object being imaged are obtained by scanning ultrasonic signals along the entire cross section, the method comprising the steps of: adaptively superposing at least two of the plurality of successive frames of the two-dimensional image data one on another so that time sequential information among the plurality of successive frames is present and displaying the superposed two-dimensional image data.

In the invention, a temporal change in motion of a cardiac muscle or the like can be displayed on the same screen. The transition of motion from the past to the present can be expressed more clearly. An area in an image defined with each pair of contour lines of the endocardium or epicardium of a cardiac muscle that is a tissue can provide velocity information. Compared with an approach in which a real-time image is visually checked or an approach in which an image resulting from a combination of tracing a contour in a B-mode image and coloring is observed, which is employed in a known tissue Doppler imaging system, hypofunction of an organ or an abnormal region can be recognized readily and easily. Moreover, the reliability of diagnosis and the patient throughput can be improved, and operator's time and labor can be saved. Furthermore, since tracing a contour of a tissue is unnecessary, signal processing will not become complex. The present invention can be realized with relatively simple circuitry.

DESCRIPTION OF THE PREFERRED EMBODIMENTS

First Embodiment

Referring to FIGS. 1 to 6, a first embodiment of the present invention will be described. A diagnostic ultrasound system of the present invention according to this embodiment is designed to produce images of tissues such as cardiac muscles or vascular walls by performing tissue Doppler imaging (TDI).

Figure 1:
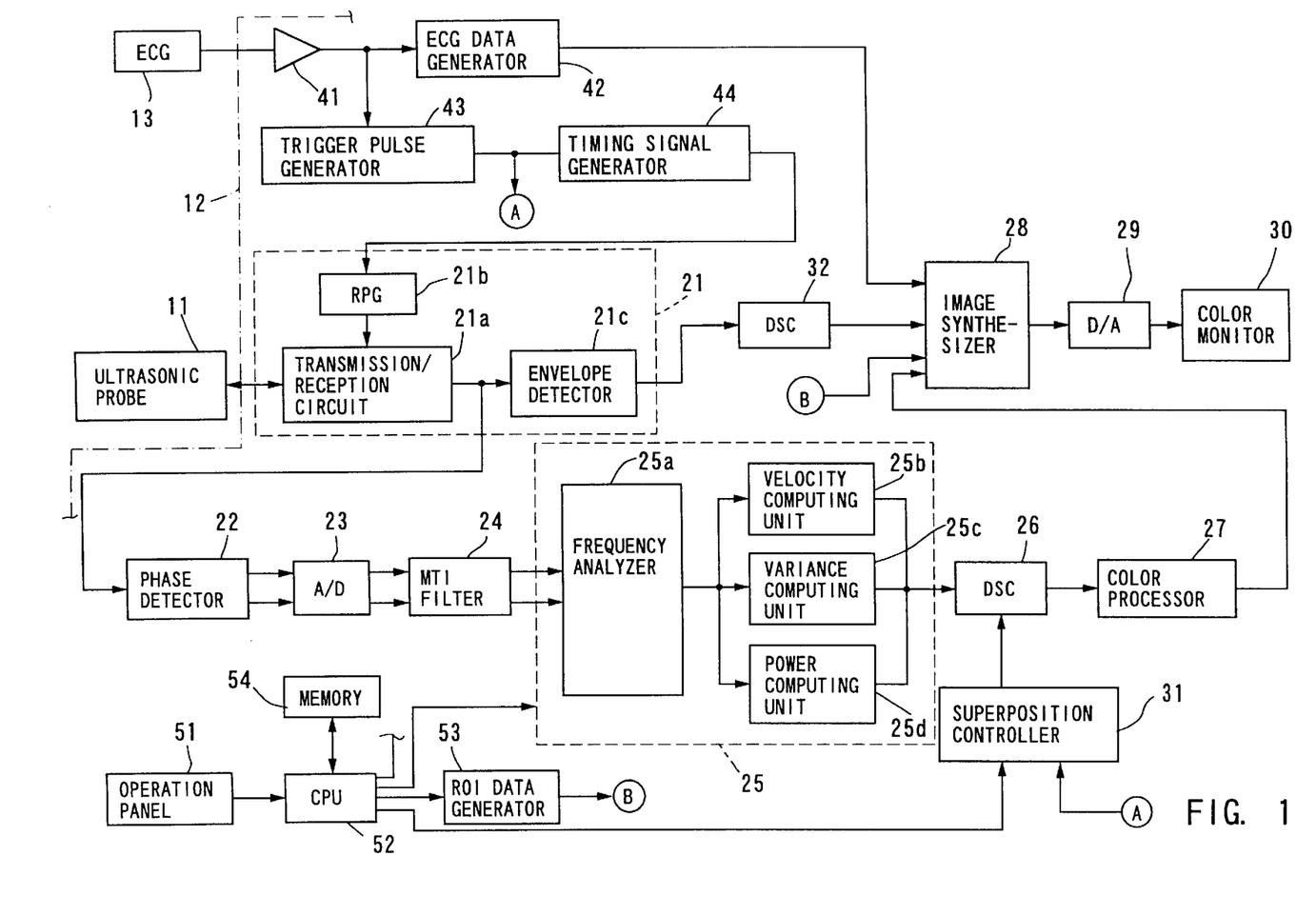
FIG. 1 is a block diagram of a diagnostic ultrasound Doppler imaging system in accordance with a first embodiment of the present invention.

FIG. 1 is a block diagram showing the configuration of the diagnostic ultrasound system. As illustrated, the diagnostic ultrasound system comprises an ultrasonic probe 11 responsible for transmission or reception of ultrasonic waves to or from a patient, a main unit 12 for driving the ultrasonic probe 11 and processing a signal received by the ultrasonic probe 11, and an electrocardiograph (ECG) 13 connected to the main unit 12 for detecting electrocardiographic information.

The ultrasonic probe 11 is of a phased array type. The main unit 12 includes a transmitter/receiver 21 connected to the ultrasonic probe 11. On the output stage of the transmitter/receiver 21, a phase detector 22, A/D converter 23, MTI filter 24, motion velocity analyzer unit 25, DSC 26, color processor 27, image synthesizer 28, D/A converter 29, and color monitor 30 are connected successively to form one channel. A superposition controller 31 that is one of major constituent features of the present invention is placed in parallel with the DSC 26. An output provided along another channel by the transmitter/receiver 21 reaches the image synthesizer 30 via another DSC 32.

The transmitter/receiver 21 drives the ultrasonic probe 11 at intervals of the cycle of a provided rate pulse, and includes a transmission/reception circuit 21a for phasing and summating echo signals sent from the ultrasonic probe 11, a rate pulse generator (RPG) 21b for providing the transmission/reception circuit 21a with necessary information such as a raster address, and an envelope detector 21c for producing a B-mode image signal.

The probe 11 is excited when driven by a pulser circuit in the transmission/reception circuit 21a, whereby ultrasonic pulsed waves are transmitted to a patient. The ultrasonic pulsed waves are reflected by tissues including the heart, and returned to the probe 11. A transducer in the probe 11 converts reflected ultrasonic waves (echoes) into voltages (echo signals), and outputs the echo signals to the transmission/reception circuit 21a.

A signal processing circuit in the transmission/reception circuit 21a delays, phases, and summates input echo signals so as to produce an echo beam signal equivalent to an ultrasonic beam focused in a scan direction. The echo beam signal resulting from phasing and summation has an envelope thereof detected.

On the output stage of the transmission/reception circuit 21a, the phase detector 22, A/D converter 23, and MTI filter 24 are connected successively. The phase detector 20 includes a mixer and low-pass filter. Echoes emanating from a tissue in motion such as a cardiac muscle or a blood flow undergo a Doppler shift (Doppler frequency) due to the Doppler effect. The phase detector 20 detects the phase of an echo signal output from the transmission/reception circuit 21a in terms of a Doppler frequency, and outputs only a Doppler signal with a detected low frequency to the MTI filter 24.

The MTI filter 24 utilizes the fact that the motion velocities of a cardiac muscle, valve, and blood flow have a relationship of "cardiac muscle<valve<blood flow" so as to remove unwanted Doppler components emanating from a blood flow and the like except a tissue in motion from the Doppler signal resulting from phase detection, and thus efficiently detects the Doppler signal emanating from a tissue lying in a direction of an ultrasonic beam. In short, the MTI filter 24 functions as a kind of low-pass filter.

The frequency analyzer unit 25 includes a frequency analyzer 25a for analyzing the Doppler frequency of each sample originating from a point on a tomographic layer according to autocorrelation or the like. Also included are a velocity computing unit 25b for computing an average Doppler frequency (average velocity) of the samples on the basis of the results of the analysis, a variance computing unit 25c for computing variance (an extent of disorder of a spectrum), and a power computing unit 25d for computing power.

The velocity, variance, and power computing units 25b to 25d can output their results of computation to the DSC 26 on the succeeding stage.

The DSC 26 not only converts image data from a format conformable to an ultrasonic scanning system to that conformable to a standard TV system but also plays a pivotal role in superposing a plurality of frame images in accordance with the present invention. The variance and power information is used to perform noise canceling on the information of an average velocity. The DSC 26 has the capability of a noise canceler, and has the configuration shown in FIG. 2 which will be described later.

The superposition controller 31 is placed in parallel with the DSC 26. Both of them cooperate with each other in the foregoing format conversion and superposition. The details will be described later.

Image data processed by the DSC 26 is sent to the color processor 27. The color processor 27 performs RGB coloring (velocities are modulated into luminance levels), in which different hues are assigned to, for example, motion directions (a direction approaching the probe and a direction receding from the probe), on image data, and sends resultant image data as TDI image data to the image synthesizer 28. At this time, the envelope detector 21c in the transmitter receiver 21 outputs a B-mode image signal. This image signal has its format converted by the B-mode DSC 32, and is supplied as B-mode image data of a digital quantity to the image synthesizer 28.

The image synthesizer 28 which includes, for example, a multiplexer, selects either TDI image data or B-mode image data for each pixel, and thus synthesizes both the data into one frame image. For pixel locations at which TDI image data (color data) resides, color data is selected as a top priority. For pixel locations at which color data does not reside, B-mode data is selected. Frame image data made by superposing a color TDI image on a black-and-white B-mode image is thus produced and sent to the color monitor 30 via the D/A converter 29. As a result, the TDI image is displayed substantially in real time against the background of the B-mode image.

Next, an ECG system will be described. The diagnostic ultrasound system includes an ECG amplifier 41 as an ECG system. An electrocardiogram (ECG) signal detected by the ECG 13 is supplied to the ECG amplifier 41. An output of the ECG amplifier 41 reaches the image synthesizer 28 by way of an ECG data generator 42, and also reaches the RPG 21 b after passing through a trigger pulse generator 43 and a timing signal in that order. An output of the trigger pulse generator 43 also reaches the superposition controller 31. The ECG data generator generates wave data defining an ECG signal, and sends the wave data to the color monitor 30 via the image synthesizer 28. The wave data is then displayed while being superposed on an image. The trigger pulse generator 43 generates a trigger pulse in response to, for example, an R wave contained in the ECG signal. A timing signal whose cycle corresponds to a very short time interval and which is synchronous with the trigger pulse is output from the timing signal generator 44. The timing signal is a signal for determining data acquisition timing, and sent to the RPG 21b.

An operation unit 51 enabling an operator in charge of a surgical procedure or an operator who operates the system to manually enter necessary information such as conditions for scanning, patient information, and ROI information is included as a component of an operation system in the diagnostic ultrasound system. Operational information entered at the operation unit 51 is passed to a CPU 52. The CPU 52 processes the information and produces delay time information and ROI information. This information is sent to circuits needing the information, whereby a desired scan can be carried out. In particular, the ROI information is sent to a ROI data generator 53. The ROI data generator 53 outputs data concerning a ROI, such as, graphic data and character data to the image synthesizer 28. The ROI then appears on an image.

Successively, the DSC 26 will be described with reference to FIG. 2. The DSC 26 includes a memory 60 placed on the input side of the DSC 26 and designed for format conversion and various kinds of computation, and an image superposition unit 61 responsible for superposition. Output data of the computing units 25b to 25d are supplied to be written in the memory 60.

The image superposition unit 61 includes a multiplier 64, which receives two inputs, on the input side of the image superposition unit. An output terminal of the multiplier 64 is connected to one input terminal of an adder 65 that receives two inputs. One input terminal of the multiplier 64 is connected to a reading side of the memory 60, while the other input terminal thereof is connected to a weighting circuit 66. The weighting circuit 66 outputs a signal associated with a changeable coefficient Kn.

An output of the adder 65 reaches the color processor 27 and also reaches a writing side of another two-dimensional memory 67. The memory 67 is included to temporarily store image data of a tomographic layer which results from pixel-by-pixel superposition. A reading-side circuit of the memory 67 is connected to one input terminal of another multiplier that receives two inputs. Another weighting circuit 69 is connected to the other input terminal of the multiplier 68. The weighting circuit 69 outputs a signal of an electrical quantity associated with a changeable coefficient Km. An output terminal of the multiplier 68 is connected to one input terminal of the adder 65. Thus, a closed loop for superposing image data of a frame on that of another frame is realized.

The superposition controller 31 for controlling superposition of image data is placed in parallel with the DSC 26. The superposition controller 31 which includes, for example, a CPU, receives a trigger pulse whose production coincides with each heart beat from the ECG system that will be described later, and can give control synchronously with the trigger pulse. The superposition controller 31 controls writing or reading of image data in or from the memory 60 located on the input side of the DSC, and also controls output of a coefficient for each pixel from the weighting circuit 66 or 69 in the image superposition unit 61, and writing or reading of image data in or from the memory 67 for temporary storage.

A computing circuit 70 acting as the aforesaid noise canceler and carrying out another computation is placed in parallel with the memory 60.

Image data is converted from one format to another through writing or reading thereof in or from the memory 60. Format-converted image data is multiplied in units of a pixel by the coefficient Kn by means of the multiplier 64. Resultant image data is then added (superposed on) to past superposed (or independent) image data by means of the adder 65. The added (superposed) data is output to the display system on the succeeding stage and temporarily stored in the memory 67. The data stored in the memory 67 is read pixel by pixel synchronously with a reading signal sent from the superposition controller 31, and then multiplied by another coefficient Km by means of the multiplier 69. The multiplied data is sent to the adder 65, and then new image data is added to (superposed on) the multiplied data.

The above superposition can be summarized as follows: assuming that an image of an immediately preceding frame already stored (superposed) in the image superposition unit 61 or superposed images ending with an image of an immediately preceding frame are old images M, and an image of a current frame to be superposed soon is a new image N, the image superposition unit 61 executes pixel by pixel superposition of data of the number of images that is calculated as follows:

$$Km \times M + Kn \times N \qquad (1)$$

where $Km \leq 1$ and $0 \leq Kn$ are weighting coefficients ($0 \leq Km$, $Kn \leq 1$, $Km+Kn=1$).

Figure 2:
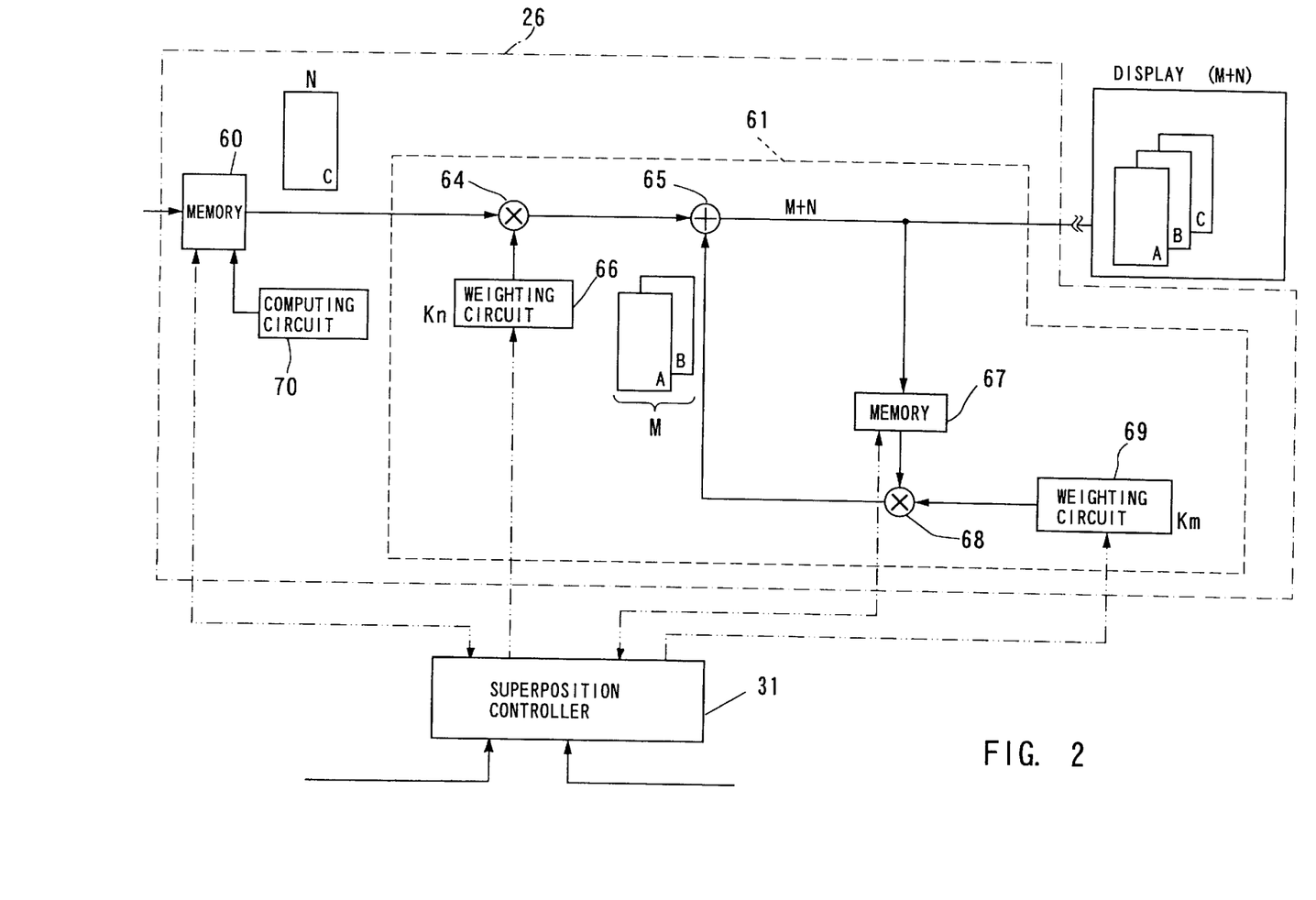
FIG. 2 is a block diagram schematically showing the configuration of a DSC.

As a result, as seen from FIG. 2 showing models of frame images, assuming that the new image N is an image of frame C and the old images M correspond to an image of one frame constructed by superposing two old frames A and B, a newly superposed image M+N is an image of one frame constructed by superposing three frames A, B, and C.

Another feature of the image superposition unit 61 will be described. Since the two weighting coefficients Km and Kn are set to have a relationship such that either of them is larger than the other (however, Km+Kn=1) in cases where pixels which represent a tissue reside in both the new and old images, priority can be given to either of the new image or old images (enhanced) in cases where pixels which represent a tissue reside in both the new and old images. To be more specific, (1) for giving priority to pixels constituting the old images M over those constituting the new image N, the coefficients are set to have a relationship of Km>Kn; and (2) for giving priority to pixels constituting the new image N over those constituting the old images M, the coefficients are set to have a relationship of Km<Kn.

For example, when Km and Kn are not equal to 0 and 1 (or 1 and 0) respectively, pixels constituting the old and new images M and N are superposed on each other at an appropriate ratio. The coefficients Km and Kn should be varied depending on a purpose of diagnosis.

By setting Km and Kn to 0 and 1 (or 1 and 0) respectively, pixels constituting either the old images M or new images N are displayed as they are. In other words, when Km is set to 1 and Kn is set to 0, pixels constituting only the old images M are displayed as they are. On the contrary, when Km is set to 0 and Kn is set to 1, pixels constituting only the new image N are displayed as they are.

The superposition is helpful especially in displaying cardiac muscles that make periodical motion. By controlling the relationship between the coefficients Km and Kn such that one of them is larger than the other, myocardial motion in opposite directions between a cardiac systole and diastole can be discerned readily.

Figure 3A:
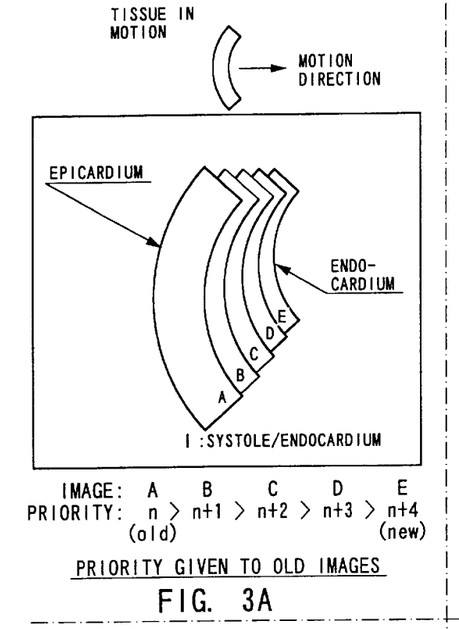
FIGS. 3A to 3D are diagrams showing models of superposed states of a tissue in motion, that is, a cardiac muscle in different superposition modes.
Figure 3B:
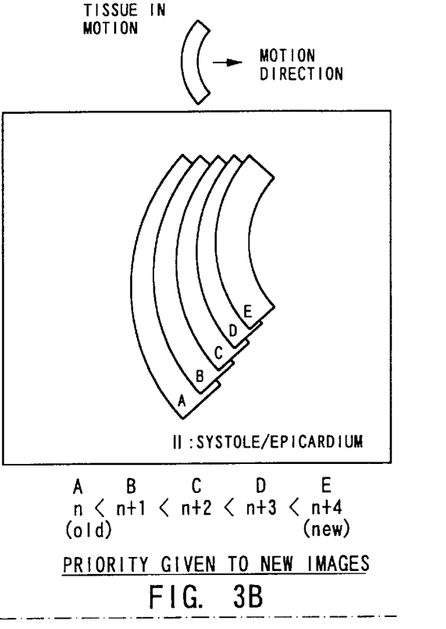
Figure 3C:
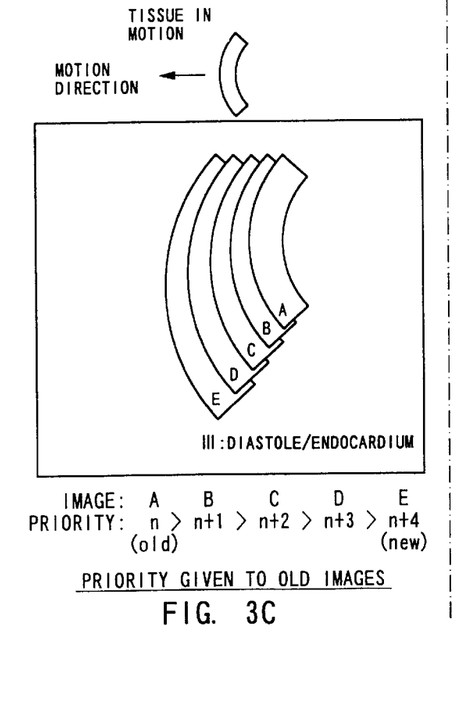
Figure 3D:
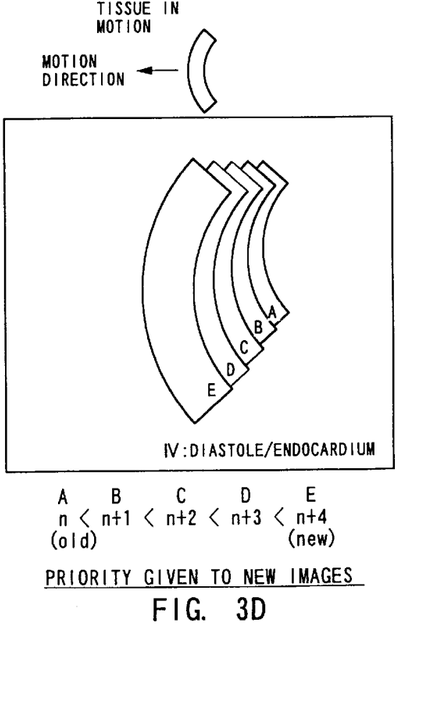

Why myocardial motion can be discerned readily will be described using the models shown in FIGS. 3A to 3D. When the systolic endocardium must be diagnosed, the coefficients in cases where pixels which represent a tissue reside in both the new and old images are set to have the relationship of Km>Kn. Thus, a superposed state in which priority is given to old images is, as shown in FIG. 3A, attained (in FIG. 3A, Km=1 and Kn=0). For assessing the motional state of the systolic epicardium, the coefficients in cases where pixels which represent a tissue reside in both the new and old images are set to have the relationship of Km<Kn. This results in, as shown in FIG. 3B, a superposed image in which priority is given to a new image. The latest epicardium is seen clearly (in FIG. 3B, Km=0 and Kn=1). For optimal diagnosis of the diastolic endocardium, the coefficients in cases where pixels which represent a tissue reside in both the new and old images are set to have the relationship of Km<Kn so that priority is, as shown in FIG. 3D, given to a new image (in FIG. 3D, Km=0 and Kn=1). For diagnosing the diastolic epicardium, the coefficients in cases where pixels which represent a tissue reside in both the new and old images are set to have the relationship of Km>Kn so that priority is, as shown in FIG. 3C, given to old images (in FIG. 3C, Km=1 and Kn=0). When a cardiac muscle makes motion, the endocardium or epicardium over the cardiac muscle can be displayed time-sequentially continually.

The superposition controller 31 is responsible for setting and changing of the weighting coefficients Km and Kn. An example of the control will be described later in conjunction with FIG. 5. The values of the coefficients Km and Kn are not necessarily limited to 0 or 1 but may be decimal numbers in the range from 0 to 1.

Next, an example of an action of an image superposition facility of the diagnostic ultrasound system will be described with reference to FIGS. 3 to 6. The image superposition facility is of great clinical value for assessment of tissues making periodical motion such as the heart. The description below will proceed on the assumption that the heart is an object region.

As shown in FIG. 3, in the case of the heart, a total of four superposition modes are conceivable in terms of whether a phase in the cardiac cycle is systolic or diastolic and whether priority is given to the endocardium or epicardium. Namely, FIG. 3A: superposition mode I
systole, priority given to endocardium (old images)

FIG. 3B: superposition mode II
systole, priority given to epicardium (new image)

FIG. 3C: superposition mode III
diastole, priority given to epicardium (old images)

FIG. 3D: superposition mode IV
diastole, priority given to endocardium (new image)

Figure 4:
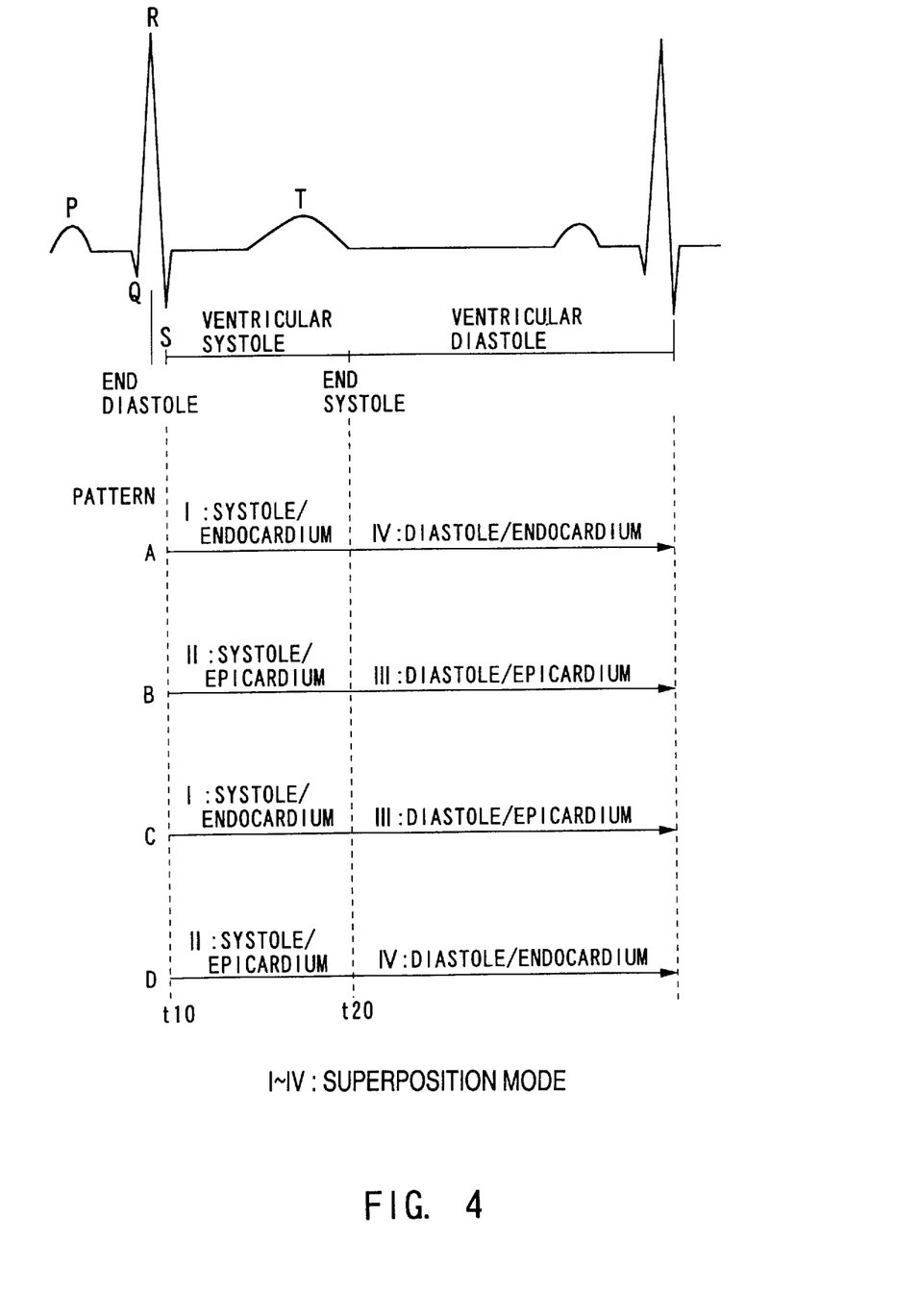
FIG. 4 is a diagram showing a combination of superposition modes within one cardiac cycle.

For scanning and displaying the heart continually over systole through diastole, four patterns A to D are, as shown in FIG. 4, conceivable as combinations of modes I to IV. That is to say, Pattern A: combination of superposition modes I and IV Pattern B: combination of superposition modes 11 and III Pattern C: combination of superposition modes I and III Pattern D: combination of superposition modes 11 and IV Whichever of the patterns is adopted for superposition is commanded at the operation unit 51 by an operator who operates the system (or an operator in charge of a surgical procedure) according to a diagnostic purpose. Needless to say, patterns may be switched alternately for scanning and display. Alternatively, the patterns may not be used but a systole or diastole alone may be commanded by selecting any of superposition modes I to IV.

Assume that the heart is scanned and displayed continually over a diastole through a systole according to any of patterns A to D.

The CPU 52 judges the conditions for scanning and the conditions for display from operational information entered at the operation unit 51 by an operator. Based on the result of the judgment, the CPU 52 gives a command necessary for controlling a scan to the RPG 21b and transmission/reception circuit 21a. An ultrasonic scan is then started according to, for example, the electronic sector scan method. The CPU 52 gives the superposition controller 31 a command indicating any of patterns A to D in addition to the values of the coefficients Km and Kn. Assume that pattern A (superposition modes I and IV) is commanded in order to image the endocardium mainly, and that the frequency analyzer unit 25 is commanded to execute velocity computing.

Figure 5:
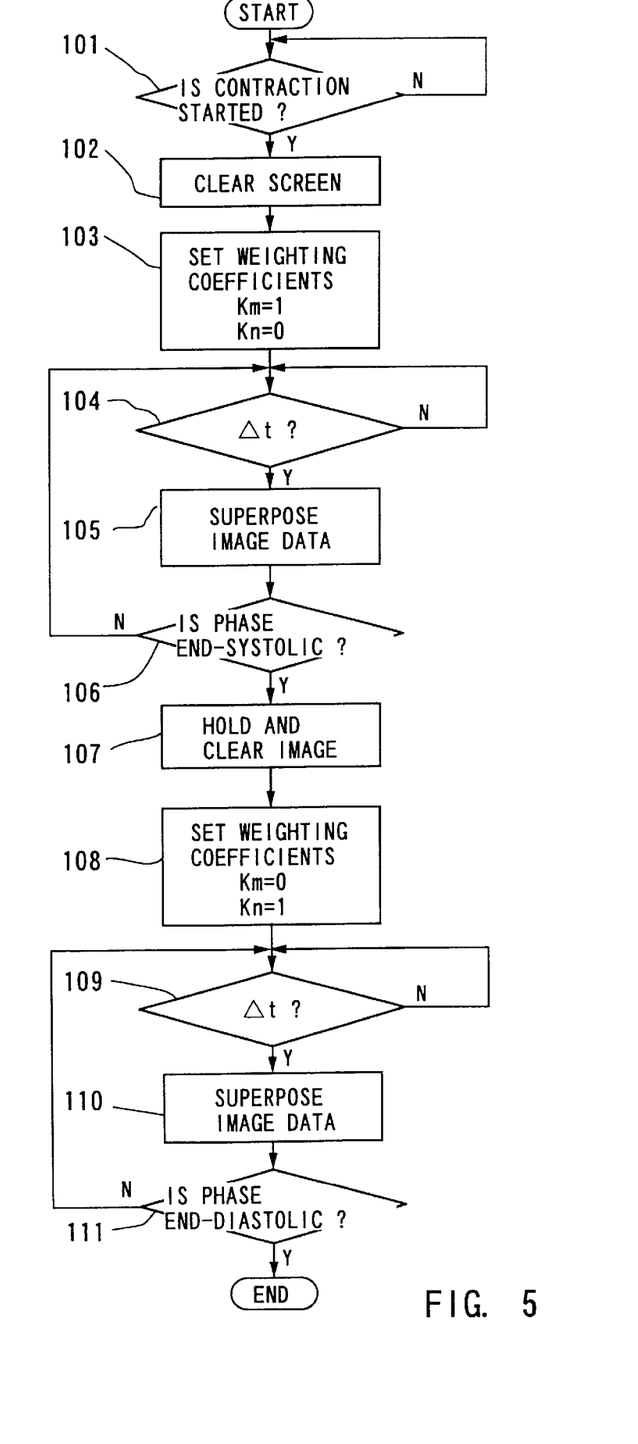
FIG. 5 is a flowchart describing an example of processing performed by a superposition controller.

The superposition control unit 31 judges whether or not a cardiac muscle starts contracting while monitoring a trigger pulse synchronous with an R wave which is output from the trigger pulse generator 43 (step 101 in FIG. 5). If the judgment is made in the negative, a standby state is retained until the start of contraction is recognized. If the judgment is made in the affirmative, an image produced with a previous heart beat (previous image) is cleared (step 102). The screen initialization is achieved by forcibly resetting pixel values in the memories 60 and 67 to zeros.

For attaining superposition mode I, the weighting circuits 66 and 69 are given commands indicating weighting coefficients Km=1 and Kn=0 respectively in cases where pixels which represent a tissue reside in both the new and old images (step 103).

Control is then passed to step 104. It is judged whether or not a Δt time (for example, 50 msec.) has elapsed since a time instant t10 at which contraction started. When the Δt time has elapsed (Yes), the superposition controller 31 commands writing or reading of image data in or from the memories 60 and 67 in the DSC 26 (step 105).

Thus, as mentioned previously, pixel values of old frame images and those of a current frame image are superposed successively. Since the weighting coefficients Km and Kn in cases where pixels which represent a tissue reside in both the new and old images are set to 1 and 0 respectively, the state in FIG. 3A in which priority is given to old images, that is, priority is given to the endocardium is attained. With the first scan after the start of contraction, as shown with t=t11 in FIG. 6, a cardiac muscle HM alone is displayed in the first TDI image.

At step 106, it is judged whether or not a trigger pulse supplied from the trigger pulse generator 43 indicates an end-systolic phase. This judgment may be carried out on the basis of a measured value of the time having elapsed after the input of a trigger pulse synchronous with an R wave. If the judgment is made in the negative, the processing of steps 104 and 105 is repeated. Once the Δt time assigned to systole is set appropriately, the second and subsequent TDI images are superposed on a past systolic TDI image. Resultant images are displayed as shown with t=t12 to t=t1m in FIG. 6. In addition to the first image of the whole of a cardiac muscle, TDI images to which the contour lines of the endocardium are added one after another are produced in color. In other words, a time-sequential change of the endocardium due to contraction during a systole is visualized in color.

Thereafter, when it is judged at step 106 that the phase is end-systolic (Yes), since the cardiac muscle will soon enter a diastole, the superposition controller 31 holds a current display image for a certain time Δt, and then clears it (step 107). The superposition controller 31 commands the weighting circuits 69 and 66 to change the values of the weighting coefficients Km and Kn in cases where pixels which represent a tissue reside in both the new and old images to 0 and 1 respectively, that is, reverse values of the previous values (step 108).

It is then judged whether or not the time Δt has elapsed since the start of relaxation (end systole) (step 109). If the judgment is made in the affirmative, superposition of image data that is the same as the aforesaid one is executed at intervals of a Δ time until contraction starts (steps 110 and 111). During a diastole, the weighting coefficients Km and Kn are changed so that priority is given to a new image (endocardium).

Figure 6:
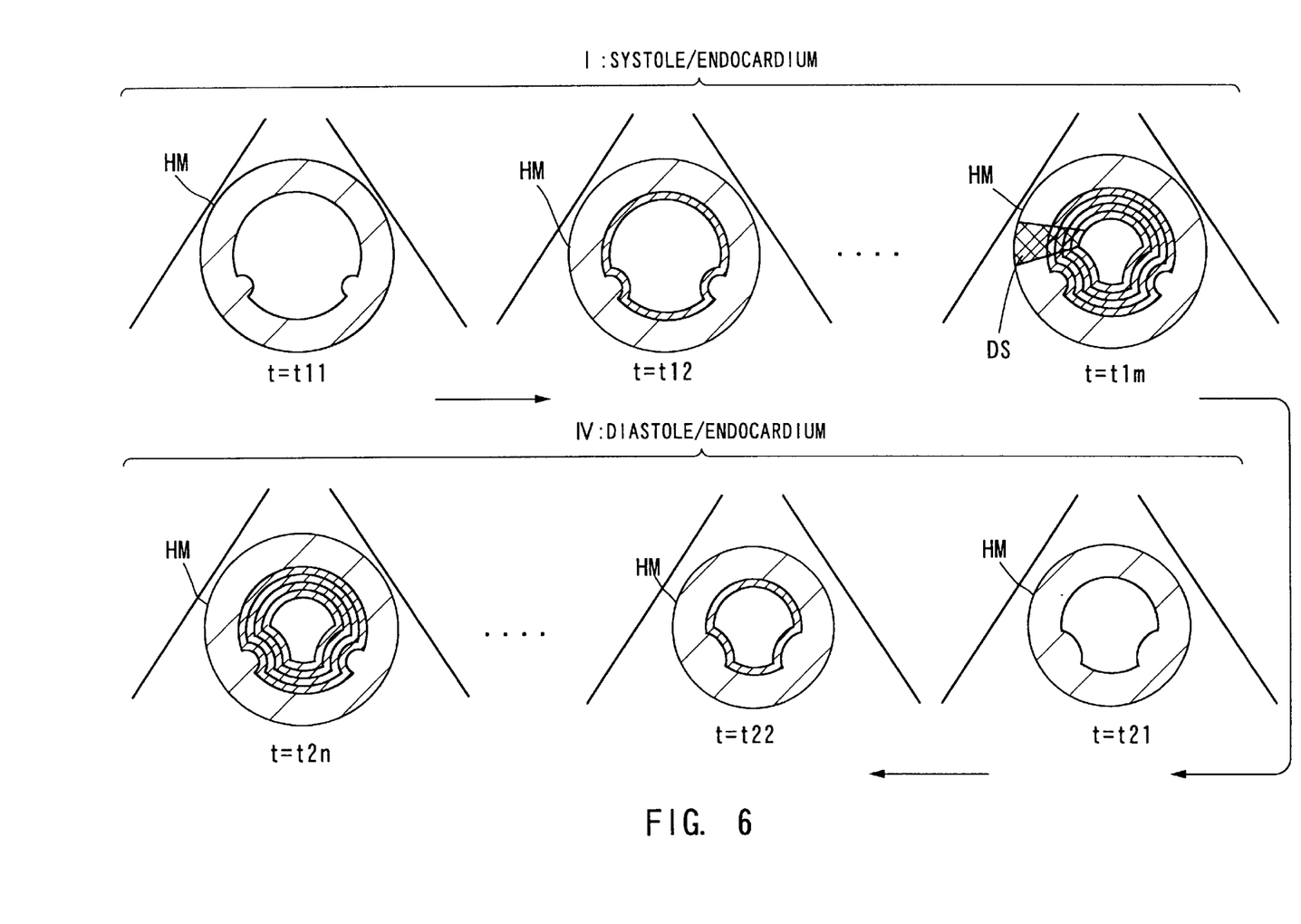
FIG. 6 is an explanatory diagram showing models of superposed display states over a systole through a diastole with priority given to the endocardium.

Displayed first during a diastole is, as shown with t=t21 in FIG. 6, a sole TDI image showing a cardiac muscle HM that has started relaxing. Thereafter, new images are, as shown with t=t22 to t=t2n in FIG. 6, added (superposed) one after another time-sequentially and displayed in color. Relaxation of the endocardium is thus visualized in color.

As mentioned above, when the display of pattern A is adopted, as shown in FIG. 6, a time-sequential TDI superposed image in which priority is given to the motion of the endocardium (change in position) made from the start of myocardial contraction to the end of relaxation can be visualized in color. If a region in a circumferential direction of the endocardium suffers from myocardial infarction, since the motion velocity of the region is small or nearly zero, the region is displayed darkly, that is, with luminance, of which level indicates a change in motion of the endocardium, held low, or expressionlessly (See part DS in an image indicated with t=t1m in FIG. 6). An operator can therefore discern the presence of an abnormal region merely by looking at the superposed TDI image. Thus, a diagnostically very useful tool is made available.

For diagnosing the epicardium, pattern B shown in FIG. 4 is commanded. For looking over the epicardium or endocardium, pattern C or D may be commanded. The width from the margin of the endocardium or epicardium which is left as a portion on which no data is superposed is determined with the value of a cycle Δt during which superposition is commanded to be carried out.

According to this embodiment, a temporal change in motion of a cardiac muscle or the like can be displayed on the same screen. Compared with a real-time image produced by a known tissue Doppler imaging system, the transition of motion from the past to the present can be expressed more clearly. This facilitates recognition of hypofunction of an organ or an abnormal region.

This embodiment is quite advantageous over another known method (refer to the foregoing reference written by Roberto M. Lan et al., "Echocardiographic Qantification of Regional Left Ventricular Wall Motion With Color Kinesis", 1877–1885, Vol. 93, No. 10, May 15, 1996), that is, a display method in which tracing a contour in a B-mode image and coloring are combined. Specifically, since an area defined with each pair of contour lines of the endocardium or epicardium provides velocity information, the hue or luminance in the area assists in grasping the motional state of a region on the endocardium or epicardium. For example, when a bluish hue is mixed in a reddish hue, the motion in the bluish portion alone is made in an opposite direction. Eventually, the fact that the cardiac muscle has an abnormality can be recognized. When a low luminance level is detected against a whole with a high luminance level, the fact that the kinetic ability of the portion of a cardiac muscle indicated with the low luminance level has deteriorated can be recognized. In addition to the information of the morphology of the endocardium or epicardium that makes motion (morphology as motion information), a direction of motion with respect to a probe or a motion velocity can be identified from an image. This is an unprecedented advantage in terms of image diagnosis. Since tracing the contour of a cardiac muscle or the like need not be carried out, tracing precision does not count. A temporal change in motion of a tissue can be displayed on the same screen relatively easily and readily.

The aforesaid superposition of images produced over a systole through a diastole which has been described in conjunction with FIGS. 5 and 6 is a mere example. As for the way of clearing or holding an image, various processing methods are conceivable.

Second Embodiment

Next, a diagnostic ultrasound system in accordance with a second embodiment of the present invention will be described in conjunction with FIGS. 7 to 9.

This embodiment is concerned with recognition of a (original) frame image, on which no data is superposed, in the superposed display state of a TDI color image. In the case of a cardiac muscle, the same region of the endocardium or epicardium moves nearly in the same direction with respect to the probe during a systole or diastole. The region is expressed with almost the same hue (for example, red or blue) over the inside through outside of the cardiac muscle. It is sometimes hard to identify the number of a frame image contributing to a certain pixel location in a superposed TDI myocardial image. According to this embodiment, this kind of incident can be avoided. It is easy to identify the number of an original frame of which pixel is used as a pixel at a specific location in a superposed display image. That is to say, a cardiac phase during a systole or diastole can be understood easily.

Figure 7:
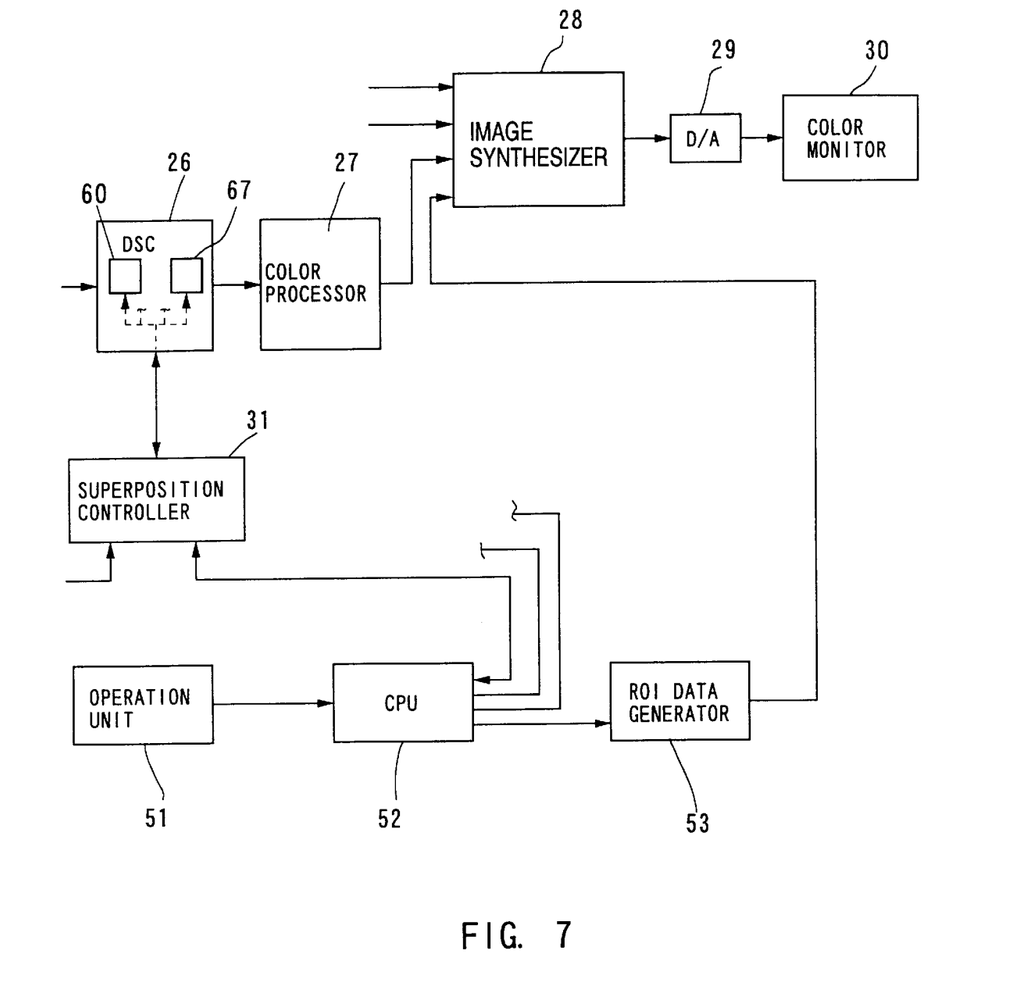
FIG. 7 is a partial block diagram of a diagnostic ultrasound Doppler imaging system in accordance with a second embodiment.

For accomplishing the above object, the diagnostic ultrasound system adopts the configuration shown in FIG. 7. This system has the same as or similar to that of the first embodiment. However, this embodiment is different from the first embodiment in terms of the way of handling image data of the superposition controller 31 and DSC 26 and the fact that the CPU 52 also executes the processing described in FIG. 8.

The superposition controller 31 can recognize the number of frame images, which have not been superposed, produced during a systole or diastole. For example, the recognition can be achieved by counting, for example, the frequency of a given time Δt. Data of a frame image number is appended pixel by pixel to image data read into the format conversion memory 60, and stored. Specifically, in the case of the first frame image, a pixel value (velocity information) and frame number data=1 are appended to each of the pixels constituting the first frame image. Image data (pixel value+frame number data) of a frame having higher priority is overwritten as it is and stored in the memory 67 on the output side. The memories 60 and 67 have a storage capacity permitting storage of pixel values and frame number data for one frame. The weighting circuits 66 and 69 and adder 65 are not involved in computing frame number data. The color processor 27 carries out coloring according only to pixel values in a superposed TDI image of one frame.

The superposition controller 31 reads image data from the memory 67 in the image superposition unit 61 in response to a command sent from the CPU 52, and interprets frame number data for each pixel.

Figure 8:
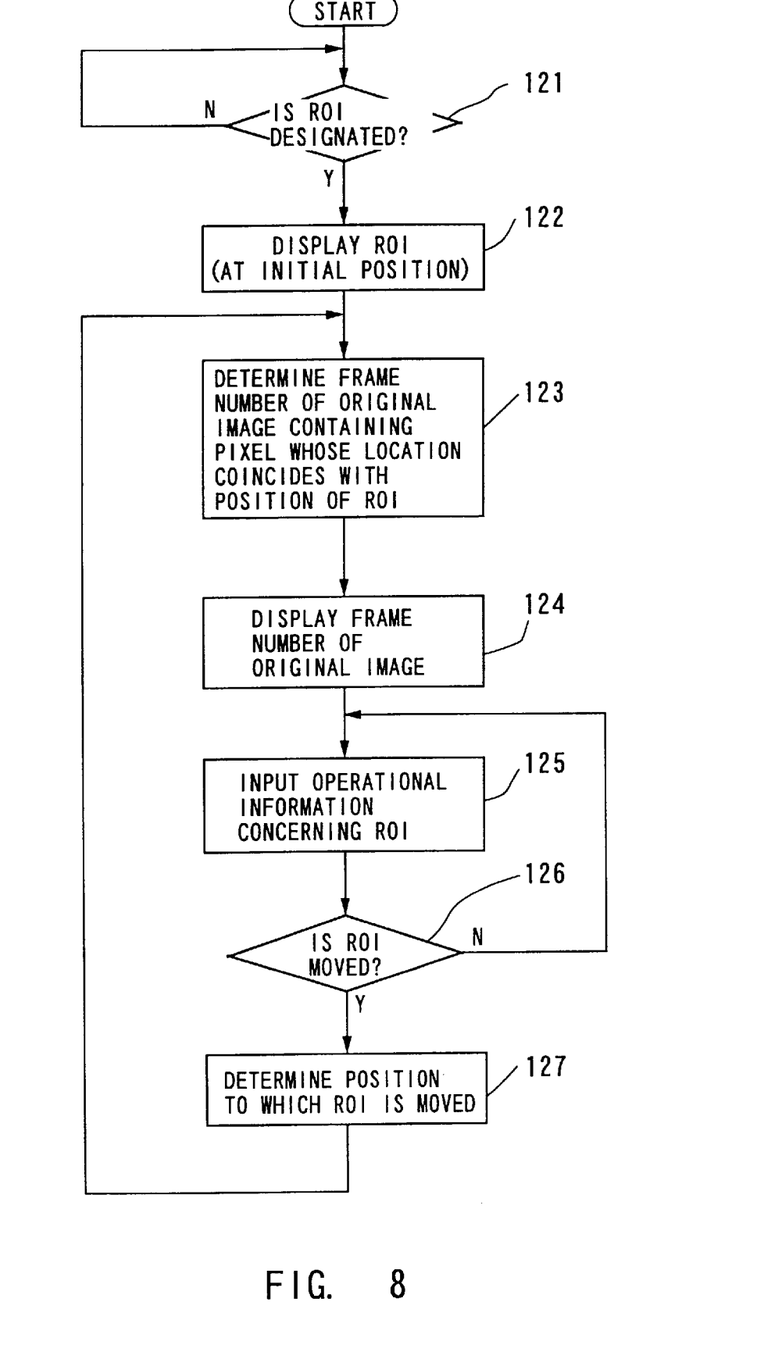
FIG. 8 is a flowchart describing processing performed by a ROI drugging facility in a CPU.

The CPU 52 carries out the processing described in FIG. 8. Specifically, it is judged from an operation signal entered at the operation unit 51 by an operator whether or not a ROI is designated (step 121). If the judgment is made in the affirmative, displaying a ROI at an initial position on a screen is commanded via the ROI data generator 53 (step 122). Herein, an X-shaped ROI is, as shown in FIG. 9, used as a ROI.

The superposition controller 31 is then commanded to determine the frame number of an original image containing the pixel whose location coincides with the position of the ROI (step 123). The superposition controller 31 then reads image data from the memory 67, checks the frame number containing the pixel whose location coincides with the position of the ROI, and returns the frame number to the CPU 52. The CPU 52 allows the ROI data generator 53 to display the determined frame number of an image (step 124).

The CPU 52 carries out the processing of steps 125 to 127. That is to say, the CPU 52 judges from operational information whether or not the ROI is moved (steps 125 and 126), and determines a position to which the ROI is moved (step 127). The processing of steps 123 and 124 is performed again on the new position of the ROI. By repeating the processing of steps 123 to 127, determination of a ROI position and display of a frame number are carried out at intervals of a given short time.

Figure 9:
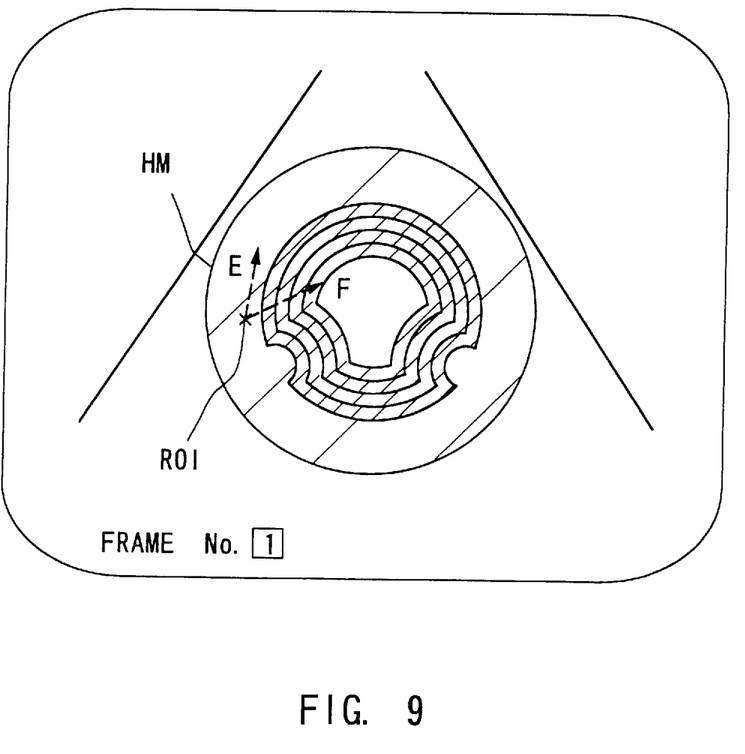
FIG. 9 is a diagram for explaining the display state of the frame number of an original image when the position of a ROI is changed.

Assume that a ROI is designated in a frozen superposed image showing an end systole (with priority given to the endocardium) shown in FIG. 9. When the position of the ROI is, as shown in FIG. 9, outermost in a myocardial superposed image, since a frame number appended to a coincident pixel is 1, the frame number "1" is displayed numerically at a given position on the monitor screen.

Assume that the ROI in this state is moved in a direction of arrow E. In this case, the position of the ROI does not come out of an annular outermost area in the myocardial image. The display of "1" does not change. However, when the ROI is moved in a direction of arrow F, the ROI advances while transversing inner annular areas of new images successively. Every time one annular area is changed to another, the display changes from "1" through "2" to "3" etc.

Thus, an operator can recognize a frame number of an original image, that is, a cardiac phase (time instant) during a systole or diastole while moving a ROI. In practice, the number of images handled for superposition and produced during a systole or diastole is determined by setting a given time Δt. By checking the display of the number of images, a phase in each cycle with which a current ROI is associated can be readily predicted, and taken into account for diagnosis. When a ROI is separated from a myocardial area and located on a background image, a numeral indicating the number of images is not displayed or a specific message appears.

When such a ROI dragging facility is also installed, even if a superposed TDI image assumes the same hue, the elapsed time of motion can be predicted and grasped readily. Thus, enrichment of the number of diagnostic facilities can be accomplished. Moreover, such frame number data of an original image (that is, phase information) can be utilized for evaluation of a superposed TDI image.

Superposition has been described by taking a system capable of real-time reproduction for instance. Even in the case of a reproduction system designed for image memory reproduction (including loop reproduction of images produced with one heart beat or a plurality of heart beats), once the aforesaid DSC 26 and superposition controller 31 are incorporated in the same manner, superposition and display can be achieved in the aforesaid various modes (patterns).

An object of ultrasonic diagnosis may be vascular walls that contract and relax with each heart beat.

In the diagnostic ultrasound Doppler imaging system, a processing circuit designed for real-time tissue Doppler imaging which is already well known may be connected in parallel with the superposition circuit.

The present invention is not limited the above configurations represented in the embodiments, and may be embodied in other specific forms without departing from the spirit or essential characteristics thereof.

What is claimed is:

1. A diagnostic ultrasound Doppler imaging system in which a plurality of successive frames of two-dimensional image data reflecting Doppler shifts caused by a tissue in motion in a cross section of an object being imaged are obtained by scanning ultrasonic signals along the entire cross section, the system comprising:

means for adaptively superposing at least two of the plurality of successive frames of the two-dimensional image data one on another to present time-sequential information from the successive frames; and means for displaying the superposed two-dimensional image data.

2. The system of claim 1, wherein said displaying means includes means for coloring the superposed two-dimensional image data according to a direction of motion of the tissue.

3. The system of claim 2, further comprising means for producing a reference signal indicative of the motion of the tissue of the object, wherein said superposing means includes means for performing a superposition process with at least two of the plurality of successive frames in synchronization with the reference signal.

4. The system of claim 3, wherein said tissue is a cardiac muscle of a heart of the objects and said reference signal is a timing signal corresponding to a specified time instant in an electrocardiogram signal wave of the heart.

5. The system of claim 4, wherein said performing means is means that performs the superposition process during at least one of a systole and a diastole of the cardiac muscle at a specified interval synchronous with the timing signal.

6. The system of claim 3, wherein said superposing means further includes means for previously storing a plurality of superposition modes for the superposition process defined on the basis of characteristics of a motion direction and a section shape of the tissue in the cross section of the object, and means for selecting a desired one from the plurality of superposition modes.

7. The system of claim 6, wherein said plurality of superposition modes depend on a superposing priority order according to either one of a temporal ascending order and a temporal descending order among the plurality of successive frames of two-dimensional image data.

8. The system of claim 6, wherein said tissue is a cardiac muscle of a patient of the object and said plurality of superposition modes comprise:

a first superposition mode giving priority of the superposition process to endocardium of the cardiac muscle during a systole thereof, a second superposition mode giving priority of the superposition process to epicardium of the cardiac muscle during the systole thereof, a third superposition mode giving priority of the superposition process to the epicardium of the cardiac muscle during a diastole thereof, and a fourth superposition mode giving priority of the superposition process to the endocardium of the cardiac muscle during the diastole thereof.

9. The system of claim 8, wherein said storing means consists of means for storing a plurality of superposition patterns made by combining at least any two modes selected from the first to fourth superposition modes for one cardiac cycle ranging from the systole to the diastole of the cardiac muscle.

10. The system of claim 1, wherein said superposing means includes means for controlling a superposition process so that at least two of the plurality of successive frames of the two-dimensional image data is adaptively superposed one on another, on the basis of an algorithm wherein pixels representing the tissue, and existing only in either one of a new superposing frame selected from the plurality of successive frames and an old frame to be superposed and formed by any of the plurality of successive frames, remain as the pixels are in the superposed two-dimensional image data, and pixels representing the tissue and commonly existing in the new and old frames, selectively remain in the superposed two-dimensional image data on a superposing priority order according to either one of a temporal ascending order and a temporal descending order of the plurality of successive frames.

11. The system of claim 10, wherein said superposition process controlling means includes a weighting circuit for performing weighting by multiplying pixel by pixel each of the successive frames of two-dimensional image data by a weighting coefficient determined depending on the algorithm.

12. The system of claim 11, wherein said weighting coefficients consist of 1 and 0.

13. The system of claim 11, further including means for changing the weighting coefficient to the opposite value when changing between the temporal ascending order and the temporal descending order.

14. The system of claim 1, wherein said superposing means consist of means for performing the superposition process with obtaining-time-phase information representing acquired time instants of the plurality of successive frames, and further comprising means for movably setting a ROI (region of interest) on an image displayed by the displaying means, and means for obtaining the time-phase information associated with an image frame providing pixels on which the ROI is set.

15. The system of claim 14, wherein said time-phase information includes numbers representing a time-sequential order of the frames of the two-dimensional image data superposed by the superposing means and said displaying means includes means for displaying the numbers together with the superposed two-dimensional image data.

16. A method of Doppler imaging for ultrasonic diagnosis in which a plurality of successive frames of two-dimensional image data reflecting Doppler shifts caused by a tissue in motion in a cross section of an object being imaged are obtained by scanning ultrasonic signals along the entire cross section, the method comprising the steps of:

adaptively superposing at least two of the plurality of successive frames of the two-dimensional image data one on another so that time-sequential information among the plurality of successive frames is present; and displaying the superposed two-dimensional image data.

17. The method of claim 16, wherein said displaying step includes coloring the superposed two-dimensional image data according to a motion direction of the tissue.

18. The method of claim 16, wherein said superposing step includes controlling the superposing process so that at least two of the plurality of successive frames of the two-dimensional image data are adaptively superposed one on another on the basis of an algorithm, wherein pixels representing the tissue, and existing only in either one of a new superposing frame selected from the plurality of successive frames and an old frame to be superposed and formed by any of the plurality of successive frames, remain as the pixels are in the superposed two-dimensional image data, and pixels representing the tissue and commonly existing in the new and old frames, selectively remain in the superposed two-dimensional image data on a superposing priority order according to either one of a temporal ascending order and a temporal descending order of the plurality of successive frames.

19. The system of claim 1, wherein said superposing means comprises:

means for previously storing a plurality of superposition modes for the superposition process defined on the basis of characteristics of a motion direction and a section shape of the tissue in the cross section of the object, and means for selecting a desired one from the plurality of superposition modes.

20. The system of claim 19, wherein said plurality of superposition modes depend on a superposing priority order according to either one of a temporal ascending order and a temporal descending order among the plurality of successive frames of two-dimensional image data.

* * * * *

UNITED STATES PATENT AND TRADEMARK OFFICE
CERTIFICATE OF CORRECTION

PATENT NO. : 5,860,927
DATED : January 19, 1999
INVENTOR(S) : Fumiyasu SAKAGUCHI et al.

It is certified that error appears in the above-identified patent and that said Letters Patent is hereby corrected as shown below:

Claim 4, Column 15, line 4, "objects" should read --object,--.

Signed and Sealed this

Second Day of November, 1999

Attest:

Q. TODD DICKINSON

Attesting Officer

Acting Commissioner of Patents and Trademarks